United States Patent
Rennich

(10) Patent No.: US 7,473,261 B2
(45) Date of Patent: Jan. 6, 2009

(54) EXTERNAL INCONTINENCE CLAMP

(76) Inventor: Henry Rennich, 23 Scandia Point NW, Calgary (CA) T3L 1T6

( * ) Notice: Subject to any disclaimer, the term of this patent is extended or adjusted under 35 U.S.C. 154(b) by 696 days.

(21) Appl. No.: 11/162,757

(22) Filed: Sep. 21, 2005

(65) Prior Publication Data
US 2006/0009793 A1 Jan. 12, 2006

(51) Int. Cl.
A61B 17/08 (2006.01)
A61F 5/48 (2006.01)

(52) U.S. Cl. .................. 606/157; 128/885; 606/201

(58) Field of Classification Search ............. 606/157, 606/151, 120, 217, 139; 128/885, 843; 604/322, 604/349, 385.09; 600/29, 30, 39, 41; 24/456, 24/460; 269/287, 211, 212, 245 R
See application file for complete search history.

(56) References Cited

U.S. PATENT DOCUMENTS

| | | | |
|---|---|---|---|
| 3,147,754 A | 9/1964 | Koessler | |
| 3,766,926 A | 10/1973 | Bliss | |
| 4,275,813 A | 6/1981 | Noiles | |
| 4,458,681 A * | 7/1984 | Hopkins | 606/157 |
| 4,942,886 A | 7/1990 | Timmons | |
| 5,336,157 A | 8/1994 | Hale | |
| 5,526,803 A * | 6/1996 | Kelly | 128/95.1 |
| 5,571,125 A | 11/1996 | Chadwick | |
| 5,620,452 A | 4/1997 | Yoon | |
| 5,728,120 A * | 3/1998 | Shani et al. | 606/201 |
| 6,007,552 A | 12/1999 | Fogarty et al. | |
| 6,681,971 B2 * | 1/2004 | Laverack et al. | 224/319 |
| 2002/0111640 A1 * | 8/2002 | Krause et al. | 606/151 |
| 2004/0059354 A1 | 3/2004 | Smith et al. | |

FOREIGN PATENT DOCUMENTS

| | | |
|---|---|---|
| FR | 2598905 | 11/1987 |
| FR | 2598908 | 11/1987 |

* cited by examiner

*Primary Examiner*—Darwin P Erezo
*Assistant Examiner*—Christina Lauer
(74) *Attorney, Agent, or Firm*—Sean W. Goodwin

(57) ABSTRACT

An external incontinence clamp for stopping involuntary voiding of urine is provided. The clamp includes a first rigid member having opposed ends, each end defining a passage extending therethrough, a second rigid member having opposed ends, each end defining a passage extending therethrough, and two pins of generally u-shape. The pins are adapted to be received by the passages defined by the ends of the first rigid member and of the second rigid member so as to secure the first rigid member in a spaced and generally parallel relationship to the second rigid member. The penis is positioned between the first and second members so that the underside of the penis is in contact with the second member and the top surface of the penis is in contact with the first member, thereby stopping involuntary voiding of urine.

18 Claims, 3 Drawing Sheets

EXTERNAL INCONTINENCE CLAMP

CROSS-REFERENCE TO RELATED APPLICATION

This application claims the benefit of U.S. patent application Ser. No. 10/688,053, filed Oct. 20, 2003, now U.S. Pat. No. 6,960,218, the entirety of which is incorporated herein by reference.

FIELD OF THE INVENTION

The present invention relates generally to male incontinency devices. More particularly, relating to an external incontinency device that is clamped to a male's penis to restrict urine flow through the urethra.

DESCRIPTION OF THE PRIOR ART

Due to the anatomy of a penis, external devices that are clamped or otherwise secured to a penis can be very effective in controlling urine flow through the urethra. The urethra is a passageway through which urine travels and it is located on the under side of the penis relatively close to the skin surface. A very small amount of pressure applied to the urethra will collapse the passageway and prevent urine from flowing through. There are many know prior art devices that attempt to accomplish this to control or prevent involuntary voiding of a bladder or to prevent urine leakage.

An example of an aforementioned device is disclosed in U.S. Pat. No. 4,942,866 to Timmons. This patent discloses an external incontinency clamp having two arcuate members hinged together at one end and a releasable fastener on the opposite ends, which are adapted to receive and clamp a penis therebetween.

Similarly, U.S. Pat. No. 3,147,754 to Koessler discloses a device for controlling incontinence having a U-shaped part with a cooperating cross bar, which together serve as a clamp for a penis.

Lastly, U.S. Pat. No. 5,571,125 to Chadwick discloses a penis-clamping device including a cushioned clamp that is hinged at one end and provided with an adjustable tensioning closure device at its other end.

While the above-described devices fulfill their respective, particular objectives and requirements, the aforementioned patents do not describe an external incontinence clamp for applying an equal force across a penis to prevent the penis from slipping towards either side of a centerline of the clamp, thereby preventing inadvertent opening of the urethra causing urine leakage.

Therefore, a need exists for a new and improved external incontinence clamp that can be used for preventing involuntary voiding of a bladder by restricting urine flow through the urethra. In this regard, the present invention substantially fulfills this need. In this respect, the external incontinence clamp according to the present invention substantially departs from the conventional concepts and designs of the prior art.

SUMMARY OF THE INVENTION

In accordance with the present invention, an external incontinence clamp is provided. The clamp includes a first rigid member having opposed ends, each end defining a passage extending therethrough, a second rigid member having opposed ends, each end defining a passage extending therethrough, and two pins of generally u-shape. The pins are adapted to be received by the passages defined by the ends of the first rigid member and of the second rigid member so as to secure the first rigid member in a spaced and generally parallel relationship to the second rigid member.

In another embodiment, an external incontinence clamp for attachment to a penis for stopping involuntary voiding of urine through the urethra passage of the penis is provided. The clamp includes a first rigid member having opposed ends, each end defining a passage extending therethrough, a second rigid member having opposed ends, each end defining a passage extending therethrough, and two pins of generally u-shape. The pins are adapted to be received by the passages defined by the ends of the first rigid member and of the second rigid member so as to secure the first rigid member in a spaced and generally parallel relationship to the second rigid member. The first and second rigid members having a length of at least the width of the penis and each member includes a pad for increasing wearing comfort.

In another embodiment, an external incontinence clamp for attachment to a penis for stopping involuntary voiding of urine through the urethra passage of the penis is provided. The clamp includes a first rigid member having inwardly angled opposed ends, each end defining at least one slot extending the width thereof, a second rigid member having inwardly angled opposed angled ends, each end defining at least one slot extending the width thereof, and two pins of generally u-shape. The pins are adapted to be received by the slots defined by the ends of the first rigid member and of the second rigid member so as to secure the first rigid member in a spaced and generally parallel relationship to the second rigid member. The first and second rigid members having a length of at least the width of the penis and each member can include a pad for increasing wearing comfort.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

An object of the present invention is to provide an external incontinence clamp for stopping involuntary voiding of urine through a penis.

Another object of the present invention is to provide an external incontinence clamp that eliminates slipping of the penis to either side of the clamp to prevent the clamp from failing to stop involuntary voiding of urine through a penis.

Still a further object of the present invention is to provide an external incontinence clamp that is easy to operate and does not require removal of the clamp for urination.

Lastly, it is an object of the present invention to provide an external incontinence clamp and method of operating the same that has a low cost of manufacture with regard to both materials and labor, and which accordingly is then susceptible of low prices of sale to the consuming public, thereby making such clamp economically available to the buying public.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE INVENTION

Figure 1:
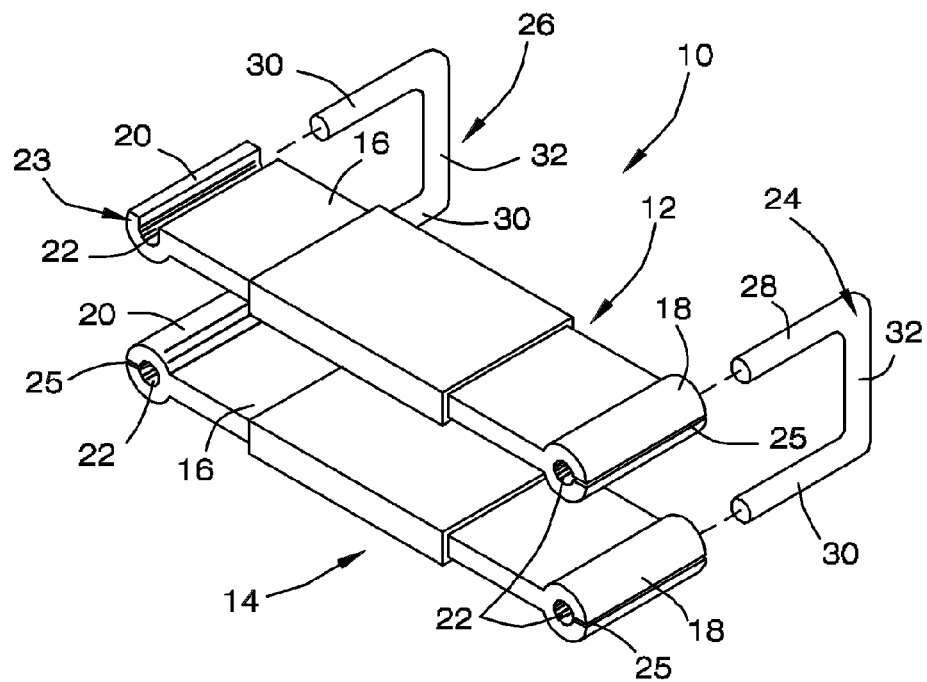
FIG. 1 is a perspective view of the preferred embodiment of the external incontinence clamp constructed in accordance with the principles of the present invention.

Referring now to the drawings, and particularly to FIGS. 1-8, a preferred embodiment of the external incontinence clamp of the present invention is shown and generally designated by the reference numeral 10.

In FIG. 1, a new and improved external incontinence clamp 10 of the present invention for preventing involuntary voiding of a bladder by restricting urine flow through the urethra of a penis is illustrated and will be described. More particularly, the external incontinence clamp 10 includes a first clamping member 12 and a second clamping member 14, which are rigid and generally rectangular shape which are coupled together in a spaced relationship by generally U-shaped connection pins 24 and 26. Each member 12 and 14 have a mid portion 16 and two ends 18 and 20. The mid portion 16 is integral with and extends between the two ends 18 and 20. Preferably, the mid portion 16 of each member 12 and 14 is substantially rectangular in shape and is rigid.

Each end 18 and 20 includes a through passage 22 that is formed along the width thereof and perpendicularly to the mid portion 16. Each passage 22 is adapted for frictionally receiving the pins 24 and 26. Preferably, the passages 22 have a circular cross-section. The ends 18 and 20 are generally cylindrically shaped and are diametrically larger than the thickness of the mid portion 16. The end 20 of the first member 12 further includes a slot 23 which formed through the end and along the passage 22. The width of the slot 23 is substantially equal to the diameter of the passage 22. The ends 18 and 20 of the second member 14 and the end 18 of the first member 12 each include a slit 25 which is formed transversely across each of the ends from the exterior surface to the passage 22. The slits 25 allow the ends 18 and 20 to expand slightly when the pins 24 or 26 are passed through the passages 22.

The pins 24 and 26 each includes a bridge 32 and two legs 28 and 30 that extend from the bridge and substantially parallel to each other. The legs 28 and 30 may be of equal or of different lengths and are adapted to be frictionally received by the passages 22. Upon inserting the pins 24 and 26 into the passages 22 of the ends 18 and 20 of the first and second clamping members 12 and 14, the members are secured together in a spaced relationship with the mid portions 16 of each clamping member being substantially parallel and with their respective ends at a fixed, spaced distance from each other.

The pins 24 and 26 are preferably stainless steel. However, one skilled in the art will appreciate that the pins may be of other materials while still retaining the desired function of the pins without departing from the spirit and scope of the present invention. The first clamping member 12 and the second clamping member 14 can be constructed from any material that affords rigidity to the members and is also hypoallergenic and non-irritating to the skin. Preferably, the first and second members 12 and 14 are constructed from Polyvinyl chloride (PVC).

Figure 2:
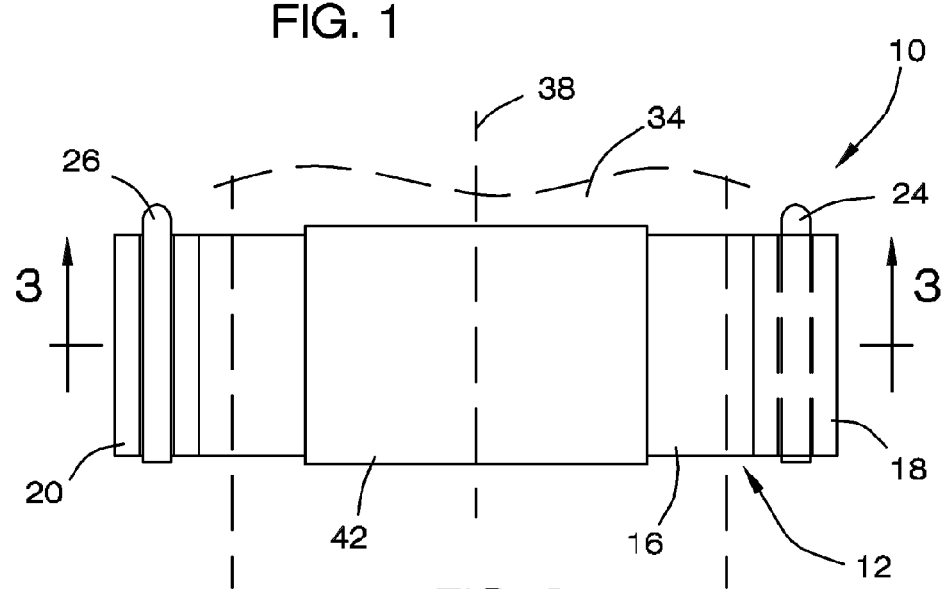
FIG. 2 is a top plan view of the external incontinence clamp of the present invention.
Figure 3:
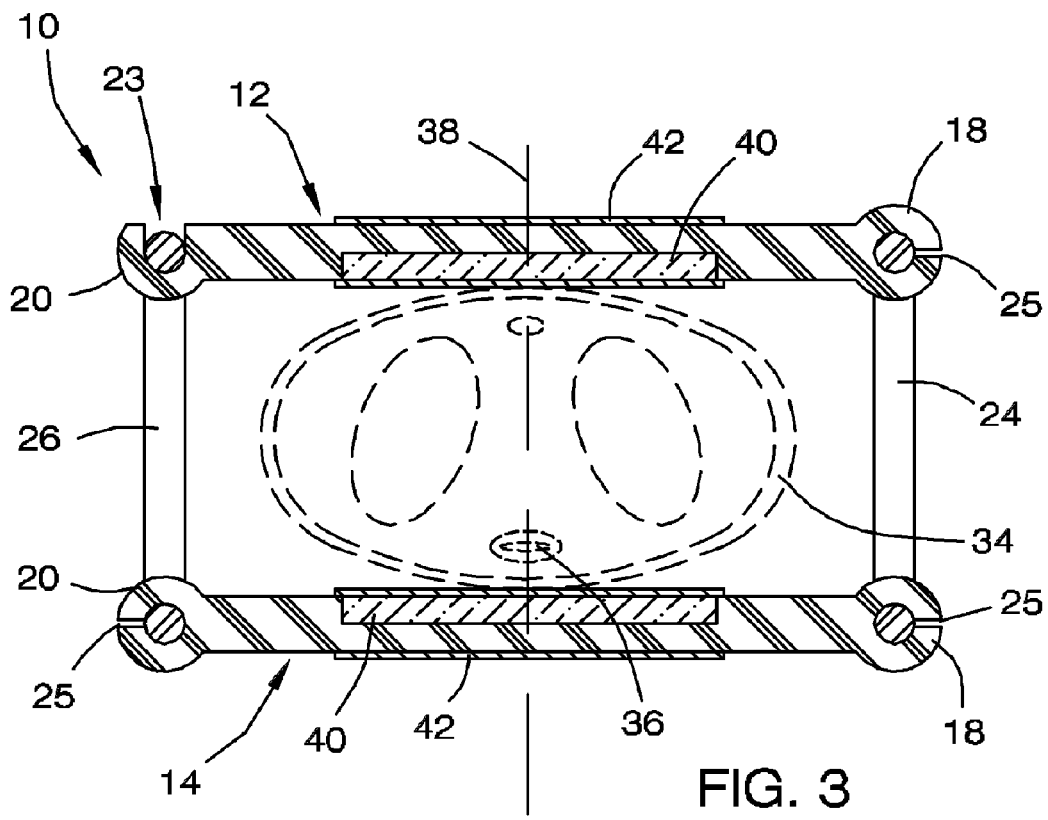
FIG. 3 is a sectional view taken along line 3-3 in FIG. 2 of the external incontinence clamp of the present invention.

Now turning to FIGS. 2 and 3, the new and improved external incontinence clamp 10 of the present invention is illustrated in use positioned on a penis 34. The penis 34 is drawn in broke-line and only a portion thereof is illustrated. The portion of the penis illustrated is a section towards the glans thereof. The penis 34 is positioned and clamped between the first clamping member 12 and the second clamping member 14 to apply pressure to the urethra passage 36, thereby preventing urine from being discharged through the penis. For the clamp 10 to properly function, the center of the urethra passage 36 must be placed as close as possible to a centerline 38 of the clamp. The clamp 10, applies an equal force along the portion of the penis 34 that is in contact with the mid portions 16, thereby minimizing penis slippage to either side of the clamp.

Figure 4:
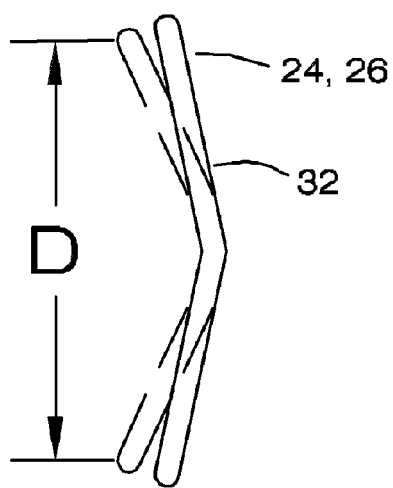
FIG. 4 is a back elevation view of an alternate embodiment of the pins a connection pin of the present invention.
Figure 5:
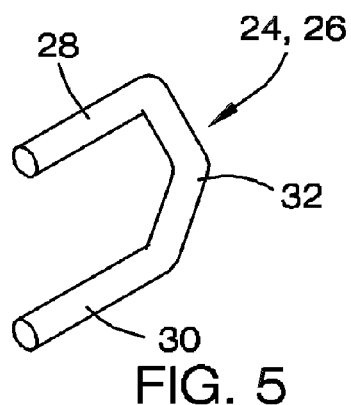
FIG. 5 is a perspective view of the connection pin shown in FIG. 4.

The amount of force applied by the clamp 10 to the penis 34 can be adjusted by varying the length of the bridge 32 of the pins 24 and 26, thereby varying the distance between the legs and between the mid portions 16. Reducing the length of the bridge 32 increases the applied force while increasing the length reduces the applied force. The length of the bridge 32 of the each pin 24 and 26 must be substantially equal so that an equal force is applied to either side of the clamped portion of the penis. The legs 28 and 30 of the pins define a space between the inner facing sides thereof. The bridge 32 can be of a length so that the defined space between the legs is at least about 0.5 inches, preferably from about 0.5 inches to about 0.75 inches. Referring to FIGS. 4 and 5, in an alternate embodiment, the pins 24 and 26 can have a bridge 32 that is slightly bent at a mid point thereof. A user to either increase or decrease the amount of applied force to the penis by the clamp 10 can adjust the degree of the bend of the bridge 32, thereby increasing or decreasing the distance D between the legs of the pin. By increasing the bend degree, the applied force is increased and reducing the bend degree, the force is decreased.

Figure 8:
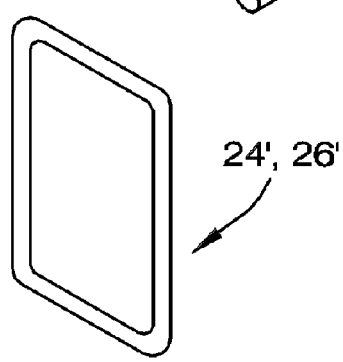
FIG. 8 is a perspective view of a connection ring.
Figure 6:
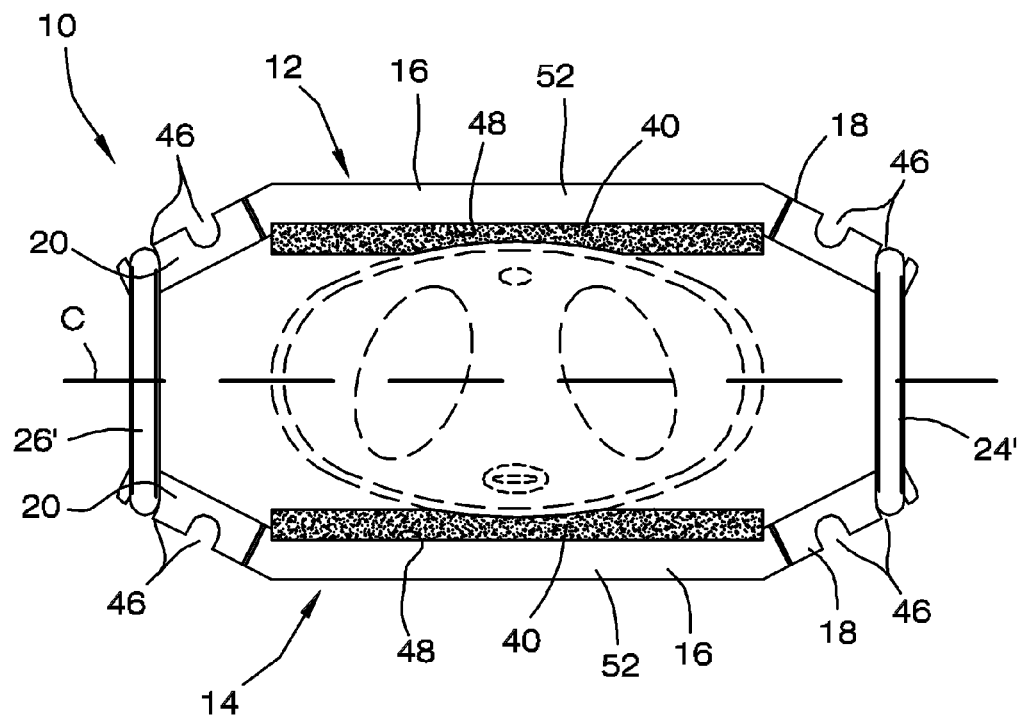
FIG. 6 is a front elevation view of an alternate embodiment of the external incontinence clamp of the present invention.
Figure 7:
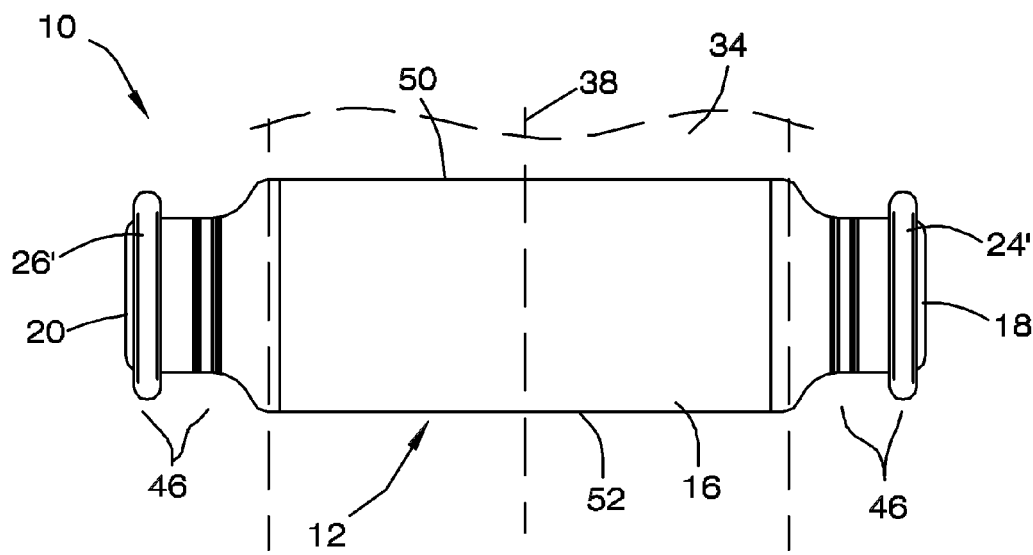
FIG. 7 is a top plan view of the alternate embodiment of the external incontinence clamp of FIG. 6.

Now turning to FIGS. 6, 7 and 8 an alternative embodiment of the incontinence clamp 10 of the present invention is illustrated in use positioned on the penis 34. In this embodiment, the opposed ends 18 and 20 of the first clamping member 12 are formed at angle in a direction inwardly of the clamp 10, and the opposed ends 18 and 20 of the second clamping member 14 are formed at an angle in a direction inwardly of the clamp. Each end 18 and 20 includes at least one slot 46 formed along the width thereof and perpendicularly to the mid portion 16. The at least one slot 46 of each opposed end 18 and 20 of each clamping member 12 and 14 is adapted for fictionally receiving a connection pin 24, 26 or alternatively a connection ring 24', 26'. Preferably, the connection rings 24', and 26' are a closed loop ring and can be rectangular in shape.

Ideally, each end 18 and 20 are of a width less than the width of each respective mid-portions 16. The reduced width of the ends 18 and 20 allows for each connection pin 24, 26 or connection ring 24', 26' to remain about flush or slightly positioned inward with respect to side edges 50 and 52 of each clamping member 12 and 14.

Each opposed end 18 and 20 of the clamping members 12 and 14 can include at least two slots 46 formed along the width thereof at spaced distances along the length of each end. In this application, a user can adjust the clamping force applied to the penis 34 by positioning the connection pins 24, 26 or connection rings 24, 26' into different slots 46. For example, as shown, the connection rings 24', 26' are received by the outwardly positioned slots 46 or in other words received by the slots which are closest to a median line C of the clamp 10, with this positioning the clamping members 12 and 14 are at their greatest spaced distance and a minimum force is applied to the penis. However, the force applied to the penis can be increased by positioning the connection rings 24', 26' into the next inwardly formed slots which reduces the spaced distance between the clamping members 12 and 14, thereby increasing the applied force. Only two slots 46 are shown formed into each opposed end 18 and 20 for exemplary purposes only, and it is noted that any number of slots may be used.

Additionally, an inner facing surface 48 of each mid portion 16 of clamping members 12 and 14 can be fitted with a pad 40 for increasing wearing comfort. The pad 40 can be of closed cell non-liquid foam that is a non-chaffing. Preferably, the pad 40 is of a shape memory foam material.

Further, the mid portions 16 of first and second clamping members 12 and 14 are of a length that is at least equal to the width of the penis 34. Preferably, the length of the mid portions 16 is slightly greater than the width of the penis 34 so that the ends 18 and 20 of the first and second clamping members 12 and 14 remain free from contact with the penis, thereby allowing enough space on either side of the penis to ensure proper blood circulation through the penis.

To position the clamp 10 on the penis 34, the first and second clamping members 12 and 14 may be initially secured together by inserting a pin 24 into the passages 22 defined by the ends 18 of the first and second members. At this point, one leg of the remaining pin 26 maybe inserted to the passage 22 defined by the end 20 of the second member 14. The penis 34 is then positioned between the first and second members, towards the glans of the penis, so that the urethra passage 36 is in close proximity to the centerline 38 of the clamp. Once the penis 34 is correctly positioned, the free leg of pin 26 is then passed through the slot 23 and frictionally snapped into the passage 22 of the end 20 of the first member 12 locking the clamp in position. To pass urine, the user simply unlocks the clamp by removing the leg of the pin 26 snapped into the slotted passage 22 of the first member 12. After urination, the user simply relocks the clamp in position by once again snapping the pin 26 back into the passage 22 of the end 20 of the first member 12.

In an additional embodiment, and for user convenience, a kit is provided having a clamp 10 including the first rigid member 12, the second rigid member 14, and a plurality of pairs of pins. At least two pairs of pins are provided where each pair of pins have different bridge length than the other pairs of pins so that a user may select a pair which provides the correct applied force to the penis. Preferably one pair has a bridge length so the defined space between the legs of the pins is about 0.5 inches, the second pair about 0.625 inches and the third pair about 0.75 inches.

While a preferred embodiment of the external incontinence clamp has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A male incontinence clamp for temporary attachment to a penis for selectively controlling the discharge of urine through the penis, the incontinence clamp comprising:
   a pair of clamping members each having opposed ends and a mid portion extending between the opposed ends, each of said opposed ends being formed at an angle in a direction inwardly of said clamp and includes at least one slot which extends along a width of said end, said pair of clamping members being arrangable generally parallel and about said penis with said opposed ends extendable past the width of the penis and with said mid portion of each clamping member contactable with said penis;
   a pair of connection pins, wherein each pin of said pair of pins includes two legs extending from a bridge portion to generally define a U-shaped pin; and
   wherein said legs of said pins are frictionally received by said slots to secure said pair of clamping members at said opposed ends and in a generally parallel and spaced distance about said penis, thereby applying a predetermined clamping force to said penis to prevent the passage of urine therethrough, and one of said pins being selectively disengaged from one clamping member to allow the passage of urine through said penis and then being reengaged to prevent passage of urine.

2. The incontinence clamp as recited in claim 1, further comprising:
   a pad secured to an inner facing surface of each of said mid portions.

3. The incontinence clamp as recited in claim 2, wherein said pad is of a foam material.

4. The incontinence clamp as recited in claim 3, wherein said pad is of a shape memory foam material.

5. The incontinence clamp as recited in claim 1, wherein said each of said opposed ends of each clamping member of said pair of clamping members includes at least two slots which extend along the width of said end.

6. The incontinence clamp as recited in claim 5, further comprising:
a pad secured to an inner facing surface of each of said mid portions.

7. The incontinence clamp as recited in claim 6, wherein said pad is of a foam material.

8. The incontinence clamp as recited in claim 7, wherein said pad is of a shape memory foam material.

9. The incontinence clamp as recited in claim 1, wherein each end of said opposed ends of each of said pair of clamping members is a width that is less than a width of each respective mid-portion.

10. A male incontinence clamp for temporary attachment to a penis for selectively controlling the discharge of urine through the penis, the incontinence clamp comprising:
a pair of clamping members each having opposed ends and a mid portion extending between the opposed ends, each of said opposed ends being formed at an angle in a direction inwardly of said clamp and includes at least two slots which extend along a width of said end at spaced distances, said pair of clamping members being arrangable generally parallel and about said penis with said opposed ends extendable past the width of the penis and with said mid portion of each clamping member contactable with said penis;
a pair connection rings, said pair of connection rings being frictionally received by said slots to secure said pair of clamping members as said opposed ends and in a generally parallel and spaced distance about said penis, thereby applying a predetermined clamping force to said penis to prevent the passage of urine therethrough, and one of said pair of connection rings being selectively disengaged from one clamping member to allow the passage of urine through said penis and then being reengaged to prevent passage of urine.

11. The incontinence clamp as recited in claim 10, wherein each ring of said pair of connection rings is a closed loop ring.

12. The incontinence clamp as recited in claim 10, further comprising:
a pad secured to an inner facing surface of each of said mid portions.

13. The incontinence clamp as recited in claim 12, wherein said pad is of a foam material.

14. The incontinence clamp as recited in claim 13, wherein said pad is of a shape memory foam material.

15. The incontinence clamp as recited in claim 10, wherein each end of said opposed ends of each of said pair of clamping members is of a width that is less than a width of each respective mid-portion.

16. A male incontinence clamp for temporary attachment to a penis for selectively controlling the discharge of urine through the penis, the incontinence clamp comprising:
a pair of clamping members each having opposed ends and a mid portion extending between the opposed ends, each of said opposed ends being formed at an angle in a direction inwardly of said clamp and includes at least two slots which extend along the width of said end at spaced distances, said pair of clamping members being arrangable generally parallel and about said penis with said opposed ends extendable past the width of the penis and with said mid portion of each clamping member contactable with said penis;
a pair connection rings, said pair of connection rings being frictionally received by said slots to secure said pair of clamping members as said opposed ends and in a generally parallel and spaced distance about said penis, thereby applying a predetermined clamping force to said penis to prevent the passage of urine therethrough, and one of said pair of connection rings being selectively disengaged from one clamping member to allow the passage of urine through said penis and then being reengaged to prevent passage of urine;
a pad of shape memory type foam secured to an inner facing surface of each of said mid portions; and
wherein each end of said opposed ends of each of said pair of clamping members is of a width that is less than a width of each respective mid-portions.

17. The incontinence clamp as recited in claim 16, wherein each ring of said pair of connection rings is a closed loop ring.

18. The incontinence clamp as recited in claim 16, wherein each ring of said pair of connection rings is a rectangular shaped closed loop ring.

* * * * *